United States Patent
Malik et al.

(10) Patent No.: US 9,528,921 B2
(45) Date of Patent: Dec. 27, 2016

(54) MATERIALS AND METHODS FOR CAPILLARY MICROEXTRACTION IN COMBINATION WITH HIGH-PERFORMANCE LIQUID CHROMATOGRAPHY COMPRISING A SOL-GEL GERMANIA TRIBLOCK POLYMER

(75) Inventors: Abdul Malik, Tampa, FL (US); Scott S. Segro, Englewood, FL (US)

(73) Assignee: UNIVERSITY OF SOUTH FLORIDA, Tampa, FL (US)

(*) Notice: Subject to any disclaimer, the term of this patent is extended or adjusted under 35 U.S.C. 154(b) by 957 days.

(21) Appl. No.: 13/641,640

(22) PCT Filed: Apr. 18, 2011

(86) PCT No.: PCT/US2011/032886
§ 371 (c)(1),
(2), (4) Date: Nov. 14, 2012

(87) PCT Pub. No.: WO2011/130737
PCT Pub. Date: Oct. 20, 2011

(65) Prior Publication Data
US 2013/0071945 A1    Mar. 21, 2013

Related U.S. Application Data

(60) Provisional application No. 61/324,995, filed on Apr. 16, 2010.

(51) Int. Cl.
*G01N 1/40* (2006.01)
*G01N 30/08* (2006.01)
(Continued)

(52) U.S. Cl.
CPC .............. *G01N 1/405* (2013.01); *B01J 20/262* (2013.01); *B01J 20/285* (2013.01); *B01J 20/286* (2013.01);
(Continued)

(58) Field of Classification Search
CPC ........ G01N 1/405; G01N 30/74; G01N 30/08; G01N 2030/009; G01N 21/33; B01J 20/286; B01J 20/285; B01J 20/262; B01J 20/264; B01J 2220/86; Y10T 436/255
See application file for complete search history.

(56) References Cited

U.S. PATENT DOCUMENTS 7,439,272 B2 * 10/2008 Xu ................................ 516/111

OTHER PUBLICATIONS

Fang, L. et aL "Germania-Based, Sol-Gel Hybrid Organic-Inorganic Coatings for Capillary Microextraction and Gas Chromatography" *Analytical Chemistry*, Dec. 15, 2007, 79(24):9441-9451.
(Continued)

*Primary Examiner* — Christopher A Hixson
(74) *Attorney, Agent, or Firm* — Saliwanchik, Lloyd & Eisenschenk (57) ABSTRACT

Germania-based sol-gel organic-inorganic hybrid coatings were prepared for on-line coupling of capillary microextraction with high-performance liquid chromatography. A germania-based sol-gel precursor, tetra-n-butoxygermane and a hydroxy-terminated triblock copolymer, poly(ethylene oxide)-block-poly(propylene oxide)-block-poly(ethylene oxide), were chemically anchored to the inner walls of a fused silica capillary (0.25 mm I.D.). Scanning electron microscopy images of the sol-gel germania triblock polymer coating were obtained to estimate the coating thickness. The analyte distribution constants between a sol-gel germania organic-inorganic hybrid coating and the samples ($K_{cs}$) were determined. For a variety of analytes from different chemical classes, including polycyclic aromatic hydrocarbons
(Continued)

HPLC Pump-Driven Extraction

(PAHs), ketones, alcohols, phenols, and amines, the $K_{cs}$ values ranged from $1.8 \times 10^1$ to $2.0 \times 10^4$. The sol-gel germania triblock polymer coatings survived exposure to high temperature solvent conditions (200° C.) with little change in extraction capabilities. Reproducibility of the method for preparation of the sol-gel germania triblock polymer coatings was also evaluated, and the capillary-to-capillary RSD values ranged from 5.3% to 6.5%. The use of higher flow rates in extraction was found to significantly reduce the time required (from 30-40 minutes to 10-15 minutes) to reach equilibrium between the sol-gel germania triblock polymer coating and the analytes in the sample solution.

19 Claims, 6 Drawing Sheets

(51) Int. Cl.
| | |
|---|---|
| *B01J 20/26* | (2006.01) |
| *B01J 20/285* | (2006.01) |
| *B01J 20/286* | (2006.01) |
| *G01N 30/74* | (2006.01) |

(52) U.S. Cl.
CPC .............. *G01N 30/08* (2013.01); *B01J 2220/86* (2013.01); *G01N 30/74* (2013.01); *Y10T 436/255* (2015.01)

(56) References Cited

OTHER PUBLICATIONS

Fan, Y. et al. "Ordered mesoporous silica coated capillary for in-tube solid phase microextraction coupled to high performance liquid chromatography" *Analytica Chimica Acta*, Jul. 6, 2005, 543(1-2):1-8.

Gallet, G. et a/. "Thermal degradation of poly(ethylene oxide-propylene oxide-ethylene oxide) triblock copolymer: comparative study by SEC/NMR, SEC/MALDI-TOF-MS and SPME/GC-MS" *Polymer*, Feb. 2002, 43(4):1081-1094.

Chong, S.L. et al. "Sol-Gel Coating Technology for the Preparation of Solid-Phase Microextraction Fibers of Enhanced Thermal Stability" *Analytical Chemistry*, Oct. 1, 1997, 69(19):3889-3898.

International Search Report in International Application No. PCT/US2011/032886, filed Apr. 18, 2011.

* cited by examiner

MATERIALS AND METHODS FOR CAPILLARY MICROEXTRACTION IN COMBINATION WITH HIGH-PERFORMANCE LIQUID CHROMATOGRAPHY COMPRISING A SOL-GEL GERMANIA TRIBLOCK POLYMER

CROSS-REFERENCE TO RELATED APPLICATIONS

This application is the U.S. national stage application of International Patent Application No. PCT/US2011/032886, filed Apr. 18, 2011, which claims priority to U.S. Application No. 61/324,995, filed Apr. 16, 2010, the disclosures of each of which are incorporated herein by reference in their entirety.

BACKGROUND OF THE INVENTION

Sol-gel coatings, introduced in solid-phase microextraction (SPME) by Malik and coworkers in 1997 [1], have effectively overcome many of the drawbacks of fiber SPME [2]. Sol-gel capillary microextraction, also introduced by Malik and coworkers [3], effectively overcame the problems inherently associated with traditionally coated capillaries used for in-tube SPME [4], most notably limited thermal and solvent stability. The chemical anchoring of sol-gel coatings to the fiber [1] or inner walls of the fused silica capillary [3] is responsible for their enhanced thermal and solvent stability [1]. Sol-gel CME coatings have been effectively coupled with GC [3,5-10], capillary electrophoresis (CE) [11,12], inductively coupled plasma mass spectrometry [13,14], and high-performance liquid chromatography (HPLC) [15-21]. Sol-gel capillary microextraction coatings can easily be hyphenated on-line with HPLC [15-21], without the need to use complex desorption devices which are required to couple fiber SPME to HPLC [22]. The majority of sol-gel coatings are silica-based. Silica-based sol-gel coatings used in fiber SPME include sol-gel poly(dimethylsiloxane) (PDMS) [1], poly(ethylene glycol) (PEG) [23], calixarene [24], acrylate [25], hydroxy fullerene [26], and crown ether [27] coatings. Notable silica-based sol-gel coatings for capillary microextraction (CME) include sol-gel PDMS [3], sol-gel PEG [3,5], electrically charged sol-gels [11,12], sol-gel dendrimer [6], and sol-gel cyano-PDMS [7]. The most significant disadvantage of silica-based sol-gel coatings is the instability of the siloxane bond under acidic [28] and basic [29] conditions.

In 2007, Malik and coworkers [30] introduced the first germania-based sol-gel coatings for use in capillary microextraction. These coatings were used in conjunction with gas chromatography (GC). Like transition metal oxide-based sol-gel coatings, including sol-gel zirconia-[8], alumina-[31], and titania-[15,19,32,33] based coatings, the sol-gel germania coatings demonstrated enhanced pH stability [30]. However, the sol-gel germania-based coatings also offer the additional advantage of having similar surface chemistry to silica-based sol-gel coatings since germania is an isostructural analog of silica [34].

BRIEF SUMMARY OF THE INVENTION

The present invention provides germania-based sol-gel coating for use in capillary microextraction on-line hyphenated with high-performance liquid chromatography. In one embodiment, the coating is prepared using the germania-based sol-gel precursor, tetra-n-butoxygermane, and the hydroxy-terminated triblock polymer, poly(ethylene oxide)-block-polypropylene oxide)-block-poly(ethylene oxide). The sol-gel germania triblock polymer coating of the present invention can extract a variety of analytes from different chemical classes, ranging from polar to nonpolar, with low picomolar to low nanomolar detection limits. Most significantly, the sol-gel germania triblock polymer coatings demonstrate impressive pH stability, surviving long term (5 days) continuous exposure to 1.0 M HCl (pH ~0) and 1.0 M NaOH (pH ~14).

In this study, we evaluated the high-temperature solvent stability of sol-gel germania triblock polymer coatings. For the first time, we report the determination of analyte distribution constants between a sol-gel germania organic-inorganic hybrid coating and the samples ($K_{cs}$). In addition, to demonstrate the reproducibility for the preparation of the sol-gel germania triblock polymer coatings, we evaluated the capillary-to-capillary reproducibility. We also studied the effect of flow rate on the amount of time required for extraction equilibrium to be established between analytes in the sample solution and the sol-gel germania triblock polymer coated microextraction capillaries.

BRIEF DESCRIPTION OF THE DRAWINGS

FIG. 3: Chromatograms representing CME-HPLC-UV analysis of amines, phenols, alcohols, ketones and PAHs using a sol-gel germania triblock polymer coated capillary (A) before and (B) after 2 h exposure to ACN/H$_2$O (50/50, v/v) at 200° C. Extraction conditions: 40 cm×0.25 mm I.D. capillary, 40 minute gravity-fed extraction at room temperature. HPLC conditions: 15 cm×4.6 mm I.D. Luna C$_{18}$ column, gradient elution 50/50 ACN/H$_2$O to 80/20 ACN/H$_2$O in 10 minutes, 1 ml/minute flow rate, UV detection at 200 nm, ambient temperature. 1=m-toluidine (1.40×10$^3$ nM), 2=2,4-dichlorophenol (3.07×10$^2$ nM), 3=9-anthracenemethanol (9.60×10$^2$ nM), 4=trans-chalcone (4.80×10$^1$ nM), 5=phenanthrene (5.61×10$^1$ nM).

DETAILED DISCLOSURE OF THE INVENTION

The present invention provides germania-based sol-gel coating for use in capillary microextraction on-line hyphenated with high-performance liquid chromatography. In one embodiment, the coating is prepared using the germania-based sol-gel precursor, tetra-n-butoxygermane, and the hydroxy-terminated triblock polymer, poly(ethylene oxide)-block-poly(propylene oxide)-block-poly(ethylene oxide). The sol-gel germania triblock polymer coating of the present invention can extract a variety of analytes from different chemical classes, ranging from polar to nonpolar, with low picomolar to low nanomolar detection limits. Most significantly, the sol-gel germania triblock polymer coatings demonstrate impressive pH stability, surviving long term (5 days) continuous exposure to 1.0 M HCl (pH ~0) and 1.0 M NaOH (pH ~14).

In one embodiment, the germania-based precursor forms upon hydrolysis. In one embodiment, the germania-based precursor is a germanium alkoxide. In a specific embodiment, the germania-based precursor is tetra-n-butoxygermane, wherein n is an integer$>=1$. For example, n can be, for example, 1, 2, 3, 4, 5, 6, 7, 8, 9, 10, . . . , or 100.

In one embodiment, the triblock polymer is poly(ethylene oxide)-block-poly(propylene oxide)-block-poly(ethylene oxide) (PEO-PPO-PEO, also known as poloxamer), which has the following structure:

formed using Chrom Perfect version 3.5 (for Windows) computer software (Justice Laboratory Software, Denville, N.J.). A model 04741 Barnstead Nanopure deionized water system (Barnstead/Thermodyne, Dubuque, Iowa) was used to produce 15MΩ nanopure water for use in HPLC mobile phases and for the preparation of aqueous samples for CME. A G-560 Fisher Vortex Genie 2 (Fisher Scientific, Pittsburgh, Pa.) was used for thorough mixing of the sol solution ingredients. A Micromax 3590F microcentrifuge (Thermo IEC, Needham Heights, Mass.) was used for centrifugation (14 000 rpm, 15 682×g) to separate the precipitates from the sol solution.

Chemicals and Materials

Tetra-n-butoxygermane (TNBG) was purchased from Gelest (Morrisville, Pa., USA). Fused silica capillary (0.250 mm, I.D.) with a polyimide external coating was procured from Polymicro Technologies (Phoenix, Ariz., USA). PEO-PPO-PEO triblock polymer, benzhydrol, 9-anthracenemethanol, m-toluidine, o-toluidine, N-methylaniline, 2,6-dimethylphenol, 2,4-dichlorophenol, 2,4,6-trichlorophenol, coumarin, acenaphthene, 1,2-benzanthracene, trans-chalcone, fluorene, phenanthrene, and fluoranthene were bought from Aldrich (Milwaukee, Wis., USA). Anthracene and 4'phenylacetophenone were procured from Eastman Kodak (Rochester, N.Y., USA). Resorcinol was obtained from Spectrum (Gardena, Calif., USA). 2-naphthol was procured from Matheson, Coleman & Bell (Cincinnati, Ohio, USA). Diphenylamine was purchased from J. T. Baker (Phillipsburg, N.J., USA). Naphthalene, trifluoroacetic acid (TFA 99%) and 2-chlorophenol were procured from Acros (Morris wherein n, x, y, and z are, independently, an integer$>=1$. In a preferred embodiment, x=z.

In certain embodiments, n, x, y, and z are, independently, an integer selected from 1, 2, 3, 4, 5, 6, 7, 8, 9, 10, . . . , or 100. In certain embodiments, the triblock polymer is selected from poloxamer 188, 407, 101, 105, 108, 122, 123, 124, 181, 182, 183, 184, 185, 212, 215, 217, 231, 234, 235, 237, 238, 282, 284, 288, 331, 333, 334, 335, 338, 401, 402, or 403.

CME-HPLC experiments were conducted using a MicroTech Scientific (Vista, Calif., USA) Ultra-Plus HPLC system with a Linear UVIS 200 variable wavelength UV detector. Online data collection and processing was per- Planes, N.J., USA). HPLC-grade solvents, methylene chloride, methanol, and acetonitrile, were bought from Fisher Scientific (Pittsburgh, Pa., USA). Poly(ether ether ketone) (PEEK) tubing (1.59 mm×0.51 mm×1.52 m), Rheodyne type ferrules, and nuts (1.59 mm) were purchased from Upchurch (Oak Harbor, Wash., USA). A Luna C18 HPLC column (150 mm×4.6 mm I.D.) was purchased from Phenomenex (Torrance, Calif., USA).

Pretreatment of Fused Silica Capillary

Fused silica capillary was subjected to a pretreatment procedure involving sequential rinsing with 4 mL each of methylene chloride, methanol, and 15MΩ deionized water under nitrogen pressure (10 psi) using a homemade capillary filling/purging device [35]. At the end of this rinsing procedure, a thin film of water remained on the capillary walls. The ends of the fused silica capillary were subsequently sealed using an oxy-acetylene torch. Following this, the capillary was placed in a gas chromatograph (GC) oven and heated at 350° C. for 2 hours, then allowed to cool to room temperature. Next, using an alumina wafer, the capillary ends were cut open and it was then installed in a GC oven with one end connected to the injection port to provide a continuous helium flow through the capillary, at a rate of 1 mL/minute. The oven temperature was programmed from 40° C. to 250° C. at a rate of 5° C./minute. The capillary was maintained at 250° C. for 2 hours, then allowed to cool down to room temperature.

Sol Solution Preparation

To prepare the sol-gel germania triblock polymer coating solution, 0.15 g of hydroxy-terminated PEO-PPO-PEO triblock polymer, 80 µL of methylene chloride, and 43 µL of TNBG, and 75 µL of trifluoroacetic acid, which contained 2% deionized water, were mixed. The sol solution was then centrifuged for 4 minutes at 14 000 rpm (15 682 g), the supernatant was transferred to a clean microcentrifuge tube and used to coat a pretreated fused silica capillary (1 m).

Capillary Coating and Conditioning

The hydrothermally pretreated fused-silica capillary was installed in a nitrogen-pressure operated capillary filling/purging device [35]. The capillary was then filled with freshly prepared sol solution under nitrogen pressure (60 psi). Three drops of the sol solution were allowed to drip out of the exit end of the capillary before it was sealed with a rubber septum. Next, the nitrogen pressure was reduced to 40 psi and maintained at that level for 30 minutes while the surface-bonded sol-gel germania-triblock polymer coating was formed. Following this, while the bulk of the coating solution remained in the liquid form, the rubber septum was removed from the exit end of the capillary and the unbonded bulk portion of the sol solution was expelled from the capillary under nitrogen pressure. Finally, the capillary was purged for an additional 90 minutes under nitrogen pressure (40 psi).

Following the coating procedure, the sol-gel coated capillary was thermally conditioned to facilitate the sol-gel reactions to completion. For this, the sol-gel germania triblock polymer coated capillary was placed in a GC oven and purged with helium flow (1 mL/minute) while simultaneously programming the temperature of the oven from 40° C. to 200° C. at a rate of 1° C./minute, holding the capillary at the final temperature for an additional 4 hours. Following this, the capillary was rinsed with 8 mL of a 1:1 (v/v) mixture of methylene chloride and methanol.

Chemical reactions involved in the formation of the sol-gel germania triblock polymer Scheme 1: Reactions Involved in the Formation of the Sol-Gel Germania Triblock PEO-PPO-PEO-Coated Microextraction Capillary

Controlled Hydrolysis of the Sol-Gel Precursor (Tetra-N-Butoxygermane):

Polycondensation of the Hydrolyzed Products:

Condensation of hydroxyl-terminated poly(ethylene oxide)-block-poly(propylene oxide)-block-poly(ethylene oxide) to the evolving sol-gel network:

-continued

In Scheme 1, n, x, y, and z are, independently, an integer>=1.

Scheme 2. Chemical Anchoring of the Evolving Sol-Gel Germania Triblock Polymer Network to the Inner Walls of a Fused-Silica Capillary Bonding to Inner Wall of Fused-Silica Capillary:

surface-bonded sol-gel germania tri-block polymer coating

-continued surface-bonded sol-gel germania tri-block polymer coating

In Scheme 2, n, x, y, and z are, independently, an integer>=1.

Preparation of Aqueous Samples for CME-HPLC Analysis

Stock solutions (1 mg/mL) of the target analytes were prepared by dissolving 10 mg of each analyte into 10 mL of methanol in 20 mL glass vials. For CME, dilute aqueous samples were prepared by transferring the appropriate amount of the stock solution, using a micropipette, into volumetric flasks (100 or 250 mL), followed by filling the flask to the calibrated volume mark with nanopure deionized water (15MΩ). For hydrophobic solutes, like PAHs, further dilution in methanol prior to dilution in deionized water was required.

CME-HPLC Analysis of Aqueous Samples

A 40 cm section of the sol-gel germania triblock polymer coated capillary was installed as an external sampling loop on a six-port HPLC injection valve after fitting its ends with 3-cm sleeves of PEEK tubing (1.59 mm O.D.), nuts, and Rheodyne ferrules. Gravity-fed extraction was conducted as described in our previous work [21]. In this study, an alternative HPLC-pump driven extraction system was introduced (FIG. 1) to study the effect of sample flow rate through the capillary on the time required to reach extraction equilibrium. For this, a third HPLC pump was connected to the waste line of the six-port injection valve. Extraction was performed by pumping the sample solution through the thoroughly cleaned waste line of the six-port injection valve (in the "load" position), through the sol-gel germania triblock polymer coated capillary, and out of the injection port until an extraction equilibrium was established between the sample and the sol-gel germania triblock polymer extracting phase (typically 10-30 minutes, depending on the flow rate and the sample). Following this, the valve was switched to the "inject" position, allowing the mobile phase (ACN/H$_2$O) to desorb the analytes from the sol-gel germania triblock polymer coated capillary and transfer them to a Luna C$_{18}$ HPLC column (15 cm×4.6 mm I.D.) for separation followed by UV detection. Isocratic and gradient elution modes were utilized as appropriate for adequate separation of the analytes in the sample solutions.

Conversion of Peak Areas to Amounts Extracted (Ng)

In the tables and extraction profiles, the peak areas obtained using Chrom Perfect 3.0 software were converted to the amounts extracted, expressed in ng. To perform this conversion, known sample volumes (20 µL) of known concentrations (20 mg/L) were directly injected into the HPLC system, which corresponds to injecting 400 ng of analyte. The mean peak areas obtained for the direct injection of 400 ng of each analyte were used to calculate the mass of each analyte extracted in ng.

The sol-gel precursor underwent controlled hydrolytic polycondensation reactions to form a colloidal system (the sol) [36]. The sol subsequently was converted into a three-dimensional liquid-filled network (the gel) [36]. Tetra-n-butoxygermane served as the sol-gel precursor, hydroxy-terminated PEO-PPO-PEO served as the sol-gel active polymer, methylene chloride was used as the solvent to thoroughly dissolve all of the sol solution constituents, and trifluoroacetic acid (TFA) served as a chelating agent to control the rate of hydrolysis of the germanium alkoxide-based sol-gel precursor [37]. The reactive hydrolyzed products underwent polycondensation to produce an evolving germania-based sol-gel network. During this process, the sol-gel active terminal hydroxyl groups of the triblock polymer condensed into the growing sol-gel network forming an organic-inorganic hybrid sol-gel material. Portions of the sol-gel germania triblock polymer network growing in the vicinity of the fused silica capillary inner surface simultaneously condensed with silanol groups on the inner walls of the capillary to produce a surface-bonded sol-gel germania triblock polymer extracting phase coating.

Figure 2:
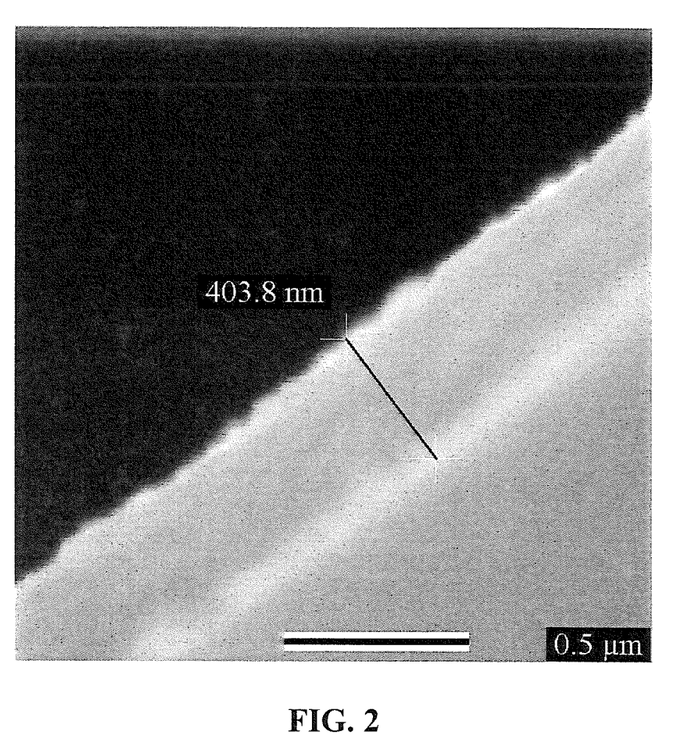
FIG. 2: Scanning electron microscopy image of the sol-gel germania triblock polymer coated microextraction capillary, magnification: 50,000×.

A scanning electron microscopy (SEM) image of the surface-bonded sol-gel germania triblock polymer coating was obtained (FIG. 2). From this SEM image, the coating thickness was estimated. The coating thickness (403.8 nm) was used, along with the length of the extraction capillary (40 cm) to calculate the volume of the sol-gel germania triblock polymer extracting phase coating ($V_c$=1.27×10$^{-7}$ L). Using the distribution equation for SPME techniques [38-40], the distribution constant ($K_{cs}$) of analyte between the sol-gel germania triblock polymer coating and sample was calculated for a wide range of analytes including PAHs, ketones, amines, alcohols, and phenols (table 1).

TABLE 1

Distribution constant ($K_{cs}$) values for PAHs, ketones, amines, alcohols, and phenols in CME-HPLC using a sol-gel germania triblock polymer coated microextraction capillary.

| Chemical Class | Chemical Name | $K_{cs}$ |
| --- | --- | --- |
| PAHs | fluorene | 3.2 × 10$^3$ |
|  | anthracene | 1.7 × 10$^4$ |
|  | fluoranthene | 1.9 × 10$^4$ |
|  | 1,2-benzanthracene | 3.7 × 10$^3$ |
|  | phenanthrene | 2.0 × 10$^4$ |
|  | naphthalene | 5.6 × 10$^3$ |
|  | acenaphthene | 2.7 × 10$^3$ |
| Ketones | coumarin | 1.2 × 10$^3$ |
|  | 4'phenylacetophenone | 1.3 × 10$^3$ |
|  | trans-chalcone | 2.4 × 10$^3$ |
| Amines | diphenylamine | 1.5 × 10$^3$ |
|  | o-toluidine | 4.2 × 10$^2$ |
|  | m-toluidine | 1.5 × 10$^2$ |
|  | N-methylaniline | 2.6 × 10$^2$ |
| Alcohols | benzhydrol | 2.0 × 10$^2$ |
|  | resorcinol | 8.1 × 10$^1$ |
|  | 2-naphthol | 1.5 × 10$^2$ |
|  | 9-anthracenemethanol | 1.0 × 10$^3$ |
| Phenols | 2-chlorophenol | 3.6 × 10$^2$ |
|  | 2,4,6-trichlorophenol | 8.2 × 10$^2$ |
|  | 2,4-dichlorophenol | 5.5 × 10$^2$ |
|  | 2,6-dimethylphenol | 1.1 × 10$^2$ |

Extraction conditions: 40 cm×0.25 mm I.D. sol-gel germania triblock polymer coated capillary, 40 minute gravity-fed extraction at room temperature. HPLC conditions: 15 cm×4.6 mm I.D. Luna C$_{18}$ column, isocratic elution with ACN/H$_2$O mobile phase, 1 ml/minute flow rate, UV detection at 200 nm for ketones, amines, alcohols, and phenols, 217 nm for naphthalene and acenaphthene, 254 nm for anthracene, phenanthrene, fluoranthene, fluorene, and 1,2-benzanthracene, ambient temperature.

To our knowledge, this is the first report on the determination of solute distribution constants for a sol-gel germania extracting phase coating. The amount extracted by the coating in capillary microextraction is given in eq. 1:

$$n = \frac{K_{cs}V_cV_s}{K_{cs}V_c + V_s}C_0 \qquad \text{Eq. 1}$$

Where, n=the amount of extracted analyte (moles), $K_{cs}$=the distribution constant of analyte between the sol-gel coating and the sample, $V_c$=the volume of the sol-gel extracting phase, $V_s$=the volume of the sample, and $C_0$=the original molar concentration of analyte in the sample. For $V_s>>K_{cs}V_c$, which holds true in CME, eq. 1 can be simplified to:

$$n=K_{cs}V_cC_0 \qquad \text{Eq. 2}$$

The amount of extracted analyte, n, was determined by comparing the peak area obtained for the extracted analyte with the peak area obtained for a known number of moles of the same analyte. The $C_0$ (original molar concentration of analyte in the sample), n, and $V_c$ values were substituted into the equation to calculate the $K_{cs}$ for each analyte, presented in table 1. Determining the $K_{cs}$ is useful in comparing extraction abilities of the sol-gel germania triblock polymer coating for different analytes since $K_{cs}$ values directly reflect extraction capabilities of the coating [34-36], unlike detection limits, which also vary according to UV absorption characteristics of the analytes. $K_{cs}$ values are also useful for determining original concentrations of target analytes [38-40].

Figure 3A:
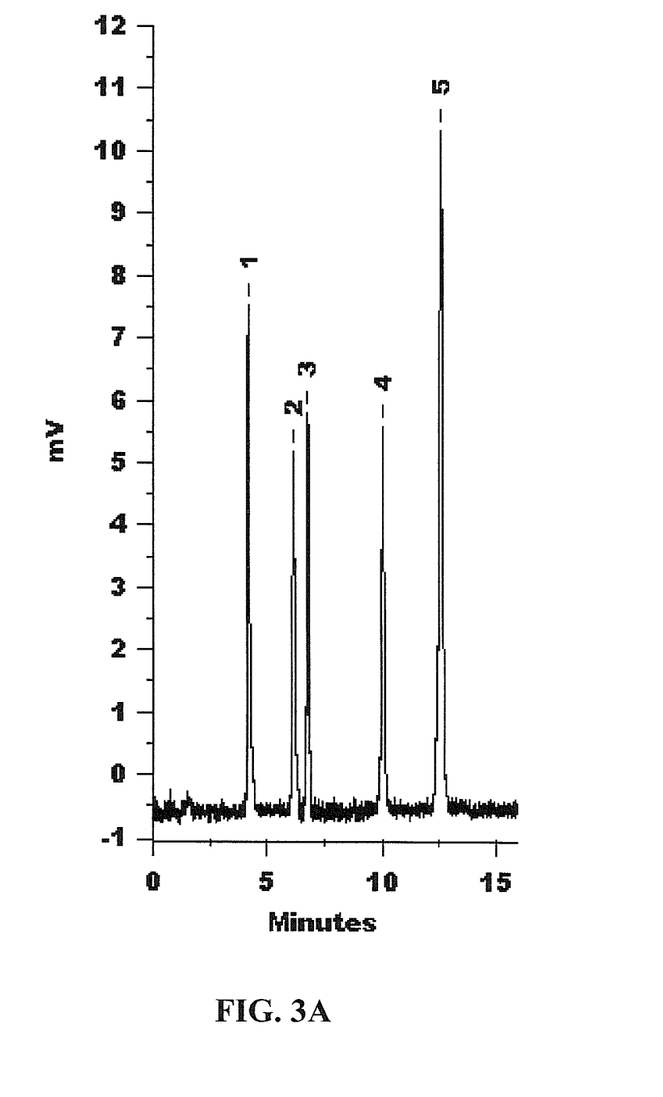
Figure 3B:
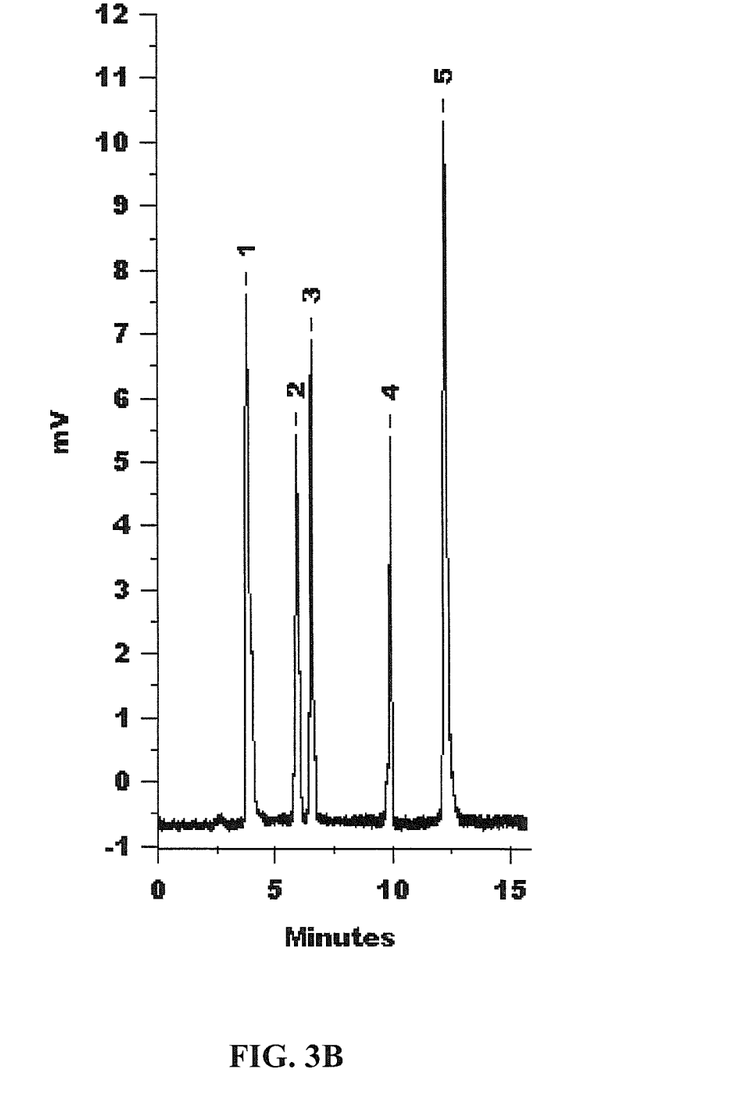

The use of high-temperature HPLC decreases the viscosity while increasing the linear velocity of $ACN/H_2O$ mobile phases, which improves peak shape while shortening run time in HPLC [41-44]. In the future, thermal gradients may replace solvent gradients in HPLC [44]. In high-temperature HPLC, the mobile phase is typically preheated in an oven to 120° C. [40-44]. Therefore, for a sol-gel coating to be successfully on-line hyphenated to a high-temperature HPLC system, it must be capable of withstanding high temperature mobile phase conditions [44]. The sol-gel germania triblock PEO-PPO-PEO polymer coated capillaries were also evaluated for stability under high temperature solvent conditions, which are used in high-temperature HPLC applications. For this, a sol-gel germania triblock polymer coated microextraction capillary was placed inside an oven heated to 200° C. as a mobile phase consisting of $ACN/H_2O$ (50/50, v/v), was pumped through it for 2 hours at a flow rate of 0.1 mL/minute. The extraction performance was evaluated before and after this treatment. The chromatograms in FIG. 3 depict the extraction of a mixture of analytes from different chemical classes before and after exposure to high temperature solvent conditions. Like the acid and base exposure [21], the high temperature solvent exposure also appeared to clean the inner surface of the sol-gel germania triblock polymer extracting phase, since slightly better extraction performance was noted after the high temperature solvent exposure as is evidenced by % increase in the peak areas of the analytes extracted after the hot solvent treatment (table 2). This is consistent with the results obtained in our previous report on high-temperature solvent resistant sol-gel polydimethyldiphenylsiloxane coatings [18]. An extraction comparison before and after exposing the sol-gel germania triblock polymer coated microextraction capillary to high temperature solvent conditions is given in table 2.

TABLE 2

Extraction comparison of PAHs, ketones, amines, alcohols, and phenols before and after exposing the sol-gel germania triblock PEO-PPO-PEO coated microextraction capillary to $ACN/H_2O$ (50/50, v/v) for 2 h at 200° C.

| Chemical class | Chemical name | Before exposure ng | After 200° C. solvent exposure ng | % Change |
|---|---|---|---|---|
| PAH | phenanthrene | 59.4 | 63.0 | 6.0 |
| Ketone | trans-chalcone | 22.1 | 22.8 | 3.2 |
| Amine | m-toluidine | 9.9 | 10.4 | 5.3 |
| Alcohol | 9-anthracenemethanol | 102.4 | 110.1 | 7.6 |
| Phenol | 2,4-dichlorophenol | 7.6 | 8.2 | 8.2 |

Extraction conditions: 40 cm×0.25 mm I.D. capillary, 40 minute gravity-fed extraction at room temperature. HPLC conditions: 15 cm×4.6 mm I.D. Luna $C_{18}$ column, gradient elution 50/50 $ACN/H_2O$ to 80/20 $ACN/H_2O$ in 10 minutes, 1 mL/minute flow rate, UV detection at 200 nm, ambient temperature, average of 3 replicate measurements.

To evaluate the reproducibility of the sol-gel coating method, capillary-to-capillary reproducibility studies were also conducted on sol-gel germania triblock polymer coated microextraction capillaries. For this, five analytes, each representing a different chemical class, were extracted on six separately prepared sol-gel germania triblock polymer coated capillaries. It was found that the preparation method for the sol-gel germania triblock polymer coated capillaries is quite reliable as is evidenced by the capillary-to-capillary HPLC peak area RSD values ranging from 5.3 to 6.5%. The capillary-to-capillary reproducibility data for analytes from each chemical class is presented in table 3.

TABLE 3

Capillary to capillary peak area reproducibility in CME-HPLC for the sol-gel germania triblock polymer coated capillaries.

| Chemical class | Chemical name peak area RSD in CME-HPLC analysis (%) (n = 6) | Capillary to capillary |
|---|---|---|
| PAH | phenanthrene | 5.6 |
| Ketone | trans-chalcone | 5.3 |
| Amine | m-toluidine | 6.5 |
| Alcohol | 9-anthracenemethanol | 6.3 |
| Phenol | 2,4-dichlorophenol | 5.3 |

Extraction conditions: 40 cm×0.25 mm I.D. sol-gel germania triblock polymer coated capillaries; 40 minute gravity-fed extraction. HPLC conditions: 15 cm×4.6 mm I.D. Luna $C_{18}$ column; gradient elution 50/50 ACN/water to 80/20 ACN/water in 10 minute; 1 mL/minute flow rate, UV detection at 200 nm for all.

Figure 1:
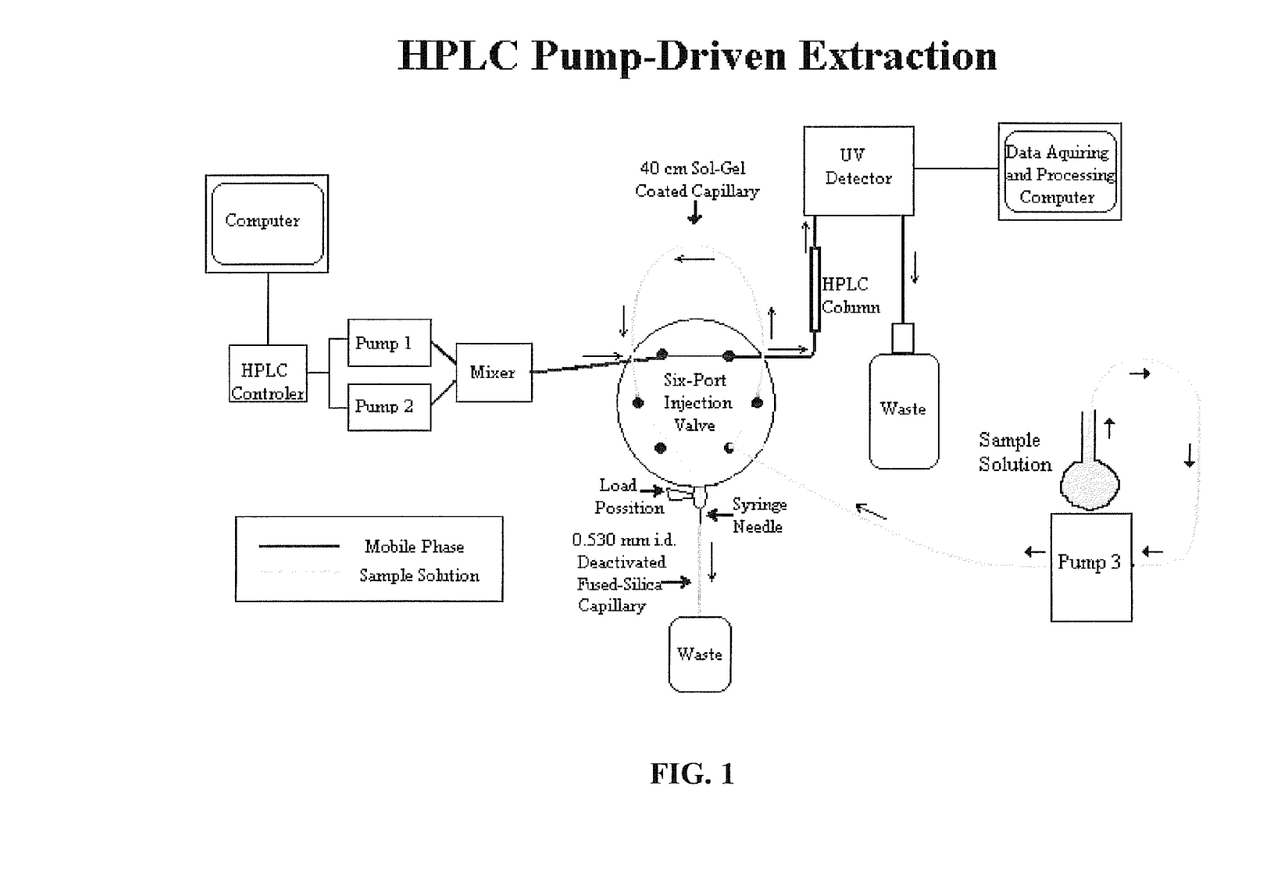
FIG. 1: Experimental setup used to carry out the CME-HPLC analysis using an HPLC pump to pass the sample through sol-gel germania triblock polymer coated capillaries. To perform extraction using enhanced flow rates, aqueous samples containing analytes are pumped using an HPLC pump into the injection valve through the thoroughly cheaned waste line, through the sol-gel germania triblock polymer coated extraction capillary, and out of the injection port to an appropriate waste container. To perform analysis, the HPLC injection valve is turned to the inject position. This allows the mobile phase to flow through the coated capillary, which desorbs the analytes and transfers them into the HPLC column for separation followed by UV detection.

In previously prepared sol-gel coatings on-line hyphenated with HPLC, a gravity-fed sample delivery system was used to perform extraction [15,17-21]. For these coatings, under gravity flow, extraction equilibrium was typically established after 30 to 80 minutes of extraction. To reduce overall analysis time, it would be desirable to shorten the amount of time required for equilibrium to be established between the analytes in the sample solution and the sol-gel coating on the inner walls of the microextraction capillary. In this study, we developed an alternative extraction configuration for capillary microextraction on-line hyphenated with HPLC and investigated the use of higher extraction flow rates (1.0 mL/minute and 2.5 mL/minute) and their effects on the amount of time required for the establishment of extraction equilibrium. To accomplish this, an HPLC pump was connected to the thoroughly cleaned waste line of the six-port HPLC injection valve (FIG. 1). Two sets of extraction experiments were performed by pumping the sample solution (which contained five analytes, representing five different chemical classes) through the sol-gel germania triblock polymer capillary at two steady flow rates: 1.0 mL/minute and 2.5 mL/minute. An HPLC pump was employed since it was capable of maintaining a constant, reproducible flow rate. The same representative analytes were extracted in triplicates at 1.0 mL/minutes for 5 minutes, 10 minutes, 20 minutes, 30 minutes, and 40 minutes and at 2.5 mL/minute for 5 minutes, 10 minutes, 15 minutes, and 20 minutes using an HPLC pump. The amounts extracted (ng) in replicate measurements at each time period were averaged and plotted against their respective extraction times. Using higher flow rates dramatically reduced the time required for the analyte extraction equilibrium to be established between the sample solution and the sol-gel germania triblock polymer coating. This is consistent with the equation proposed by Eisert and Pawliszyn for in-tube SPME (eq. 3), where it was determined that the time required for equilibrium to be established for the analytes between the sample solution and the extracting phase is inversely proportional to the flow rate of the sample solution [4], given by eq. 3:

$$t_e = \frac{L(1+k)}{u} \qquad \text{Eq. 3}$$

where $t_e$=extraction time, L=length of the capillary holding the extracting phase, k=retention factor, and u=laminar flow rate of the fluid.

Figure 4:
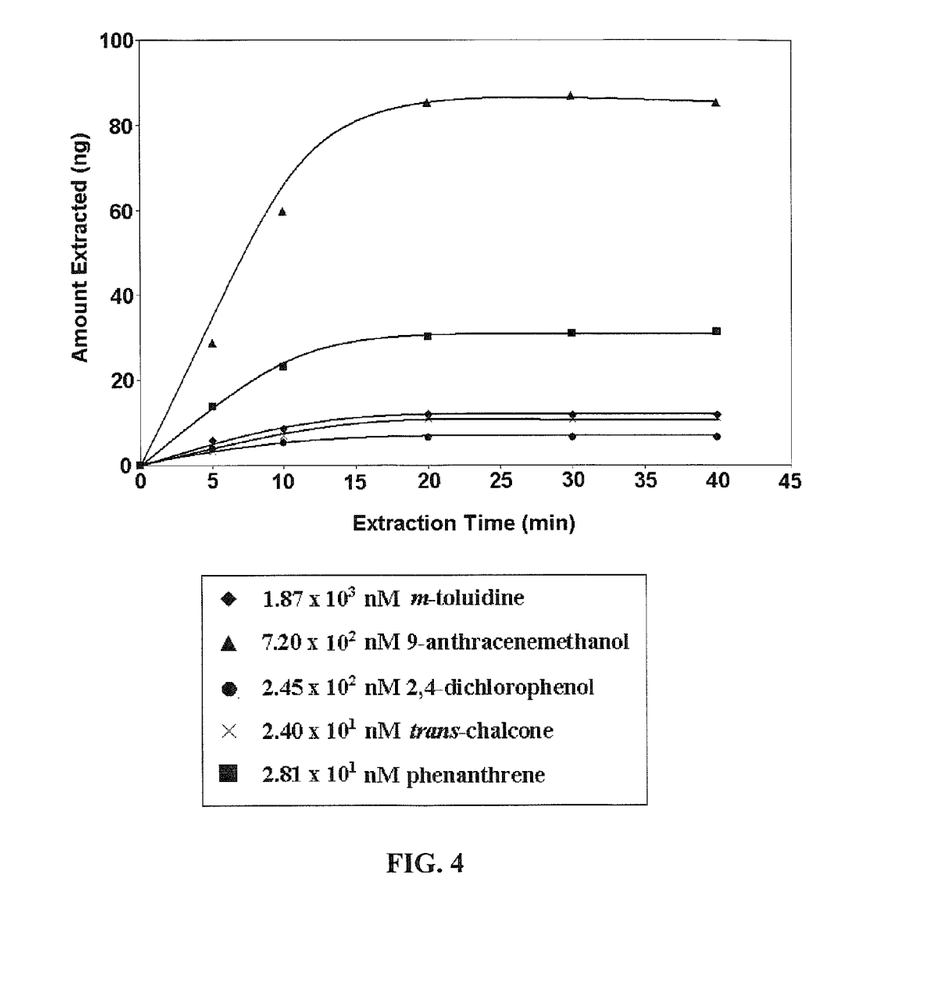
FIG. 4: Extraction profiles of m-toluidine, 3,5-dimethylphenol, 9-anthracenemethanol, trans-chalcone, and phenanthrene for the sol-gel germania triblock polymer coated capillary for HPLC pump driven extraction (1.0 mL/minute flow rate).
Figure 5:
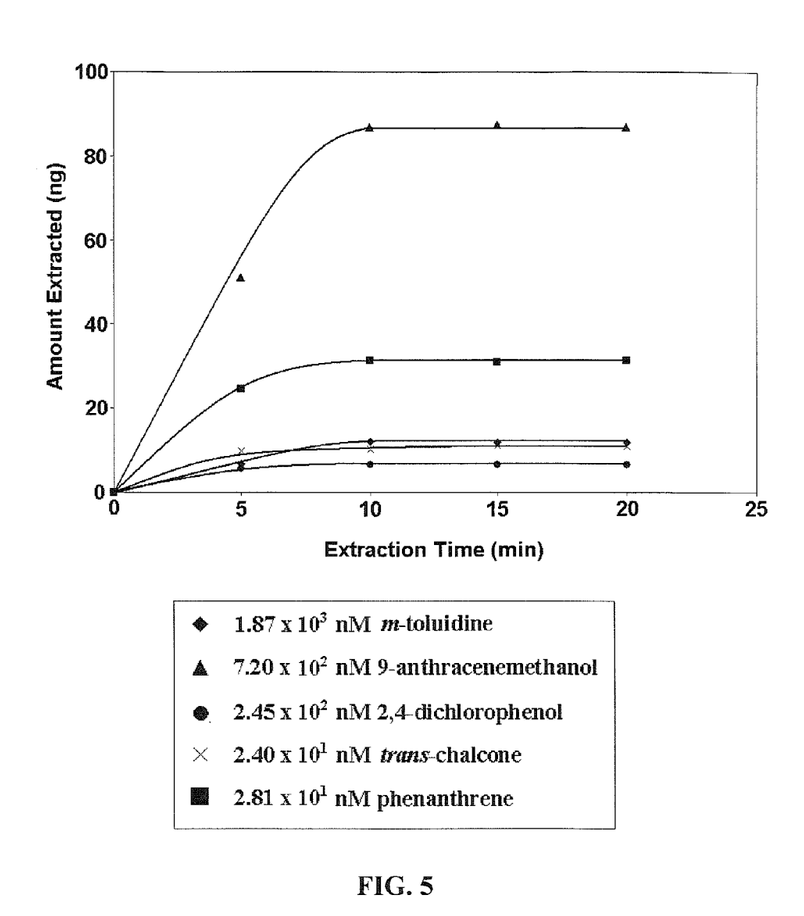
FIG. 5: Extraction profiles of m-toluidine, 3,5-dimethylphenol, 9-anthracenemethanol, trans-chalcone, and phenanthrene for the sol-gel germania triblock polymer coated capillary for HPLC pump driven extraction (2.5 mL/minute flow rate).

In our previous study on sol-gel germania triblock polymer coated capillaries [21], a mixture of five analytes, each representative of a particular chemical class (amine, phenol, alcohol, ketone, and PAH), were extracted three times each using a gravity-fed sample delivery system for 10 minutes, 20 minutes, 30 minutes, 40 minutes, 50 minutes, and 60 minutes. Under gravity-fed extraction, m-toluidine and 3,5-dimethylphenol required 30 minutes of extraction, while 9-anthracenemethanol, trans-chalcone, and phenanthrene required 40 minutes of extraction to reach equilibrium [21]. From the graph in FIG. 4, m-toluidine, 3,5-dimethylphenol, 9-anthracenemethanol, and trans-chalcone required approximately 20 minutes of extraction, while phenanthrene required 30 minutes of extraction for equilibrium to be established using a flow rate of 1.0 mL/minute. From the graph in FIG. 5, m-toluidine, 3,5-dimethylphenol, 9-anthracenemethanol, and phenanthrene required only 10 minutes of extraction, while trans-chalcone required between 10 and 15 minutes of extraction for equilibrium to be established using an extraction flow rate of 2.5 mL/minute. The use of a higher extraction flow rate can dramatically reduce the time required to reach extraction equilibrium in sol-gel capillary microextraction, and thereby speed up the analysis time.

For the first time, the high-temperature solvent resistance of a sol-gel germania coating in capillary microextraction was evaluated. It was determined that the sol-gel germania triblock polymer coated capillaries are capable of withstanding exposure to high temperature solvents (200° C.) conditions, making them suitable for possible future use in high-temperature HPLC. Also, the analyte distribution constants ($K_{cs}$) between the aqueous sample matrix and a sol-gel germania-based coating were determined for the first time. These $K_{cs}$ values ranged from $1.8 \times 10^1$ to $2.0 \times 10^4$ for biomedically and environmentally significant compounds, ranging from nonpolar to polar, including polycyclic aromatic hydrocarbons, ketones, amines, alcohols, and phenols. The method of preparation for the sol-gel germania triblock polymer coated capillaries was also determined to be quite reliable, with capillary-to-capillary reproducibility ranging from 5.3% to 6.5%. Finally, the use of higher extraction flow rates can reduce the amount of time required for analyte extraction equilibrium to be established between the sample solution and the sol-gel germania triblock polymer coating.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. S. L. Chong, D. Wang, J. D. Hayes, B. W. Wilhite, A. Malik, Anal. Chem. 69 (1997) 3889.
2. C. L. Arthur, J. Pawliszyn, Anal. Chem. 62 (1990) 2145.
3. S. Bigham, J. Medlar, A. Kabir, C. Shende, A. Alli, A. Malik, Anal. Chem. 74 (2002) 752.
4. R. Eisert, J. Pawliszyn, Anal. Chem. 69 (1997) 3140.
5. S. Kulkarni, A. M. Shearrow, A. Malik, J. Chromatogr. A 1174 (2007) 50.
6. Kabir, C. Hamlet, K. Soo Yoo, G. R. Newkome, A. Malik, J. Chromatogr. A 1034 (2004) 1.
7. S. Kulkarni, L. Fang, K. Alhooshani, A. Malik, J. Chromatogr. A 1124 (2006) 205.
8. K. Alhooshani, T. Y. Kim, A. Kabir, A. Malik, J. Chromatogr. A 1062 (2005)
9. M. Shearrow, G. A. Harris, L. Fang, P. K. Sekhar, L. T. Nguyen, E. B. Turner, S. Bhansali, A. Malik, J. Chromatogr. A 1216 (2009) 5449.
10. M. Shearrow, S. Bhansali, A. Malik, J. Chromatogr. A 1216 (2009) 6349.
11. W. Li, D. Fries, A. Malik, J. Sep. Sci. 28 (2005) 2153.
12. W. Li, D. Fries, A. Alli, A. Malik, Anal. Chem. 76 (2004) 218.
13. F. Zeng, B. Hu, Talanta 73 (2007) 372.
14. Y. Wu, B. Hu, Z. Jiang, Y. Feng, P. Lu, B. Li, Rapid Commun. Mass Spectrom. 20 (2006) 3527.
15. T. Y. Kim, K. Alhooshani, A. Kabir, D. P. Fries, A. Malik, J. Chromatogr. A 1047 (2004) 165.
16. Y. Fan, Y. Q. Feng, S. L. Da, Z. H. Wang, Talanta 65 (2005), 111.
17. S. S. Segro, A. Malik, J. Chromatogr. A 1200 (2008) 62.
18. S. S. Segro, A. Malik, J. Chromatogr. A 1205 (2008) 26.
19. S. S. Segro, Y. Cabezas, A. Malik, J. Chromatogr. A 1216 (2009) 4329.
20. S. S. Segro, A. Malik, J. Chromatogr. A. 1216 (2009) 7677.
21. S. S. Segro, J. Triplett, A. Malik, Anal. Chem. (2010) in press.
22. K. Jinno, M. Taniguchi, M. Hayashida, J. Pharm. Biomed. Anal. 17 (1998) 1081.
23. Z. Wang, C. Xiao, C. Wu, H. Han, J. Chromatogr. A 893 (2000) 157.
24. X. Li, Z. Zeng, S. Gao, H. Li, J. Chromatogr. A 1023 (2004) 15.
25. M. Liu, Z. Zeng, B. Xiong, J. Chromatogr. A 1065 (2005) 287.
26. J. Yu, L. Dong, C. Wu, L. Wu, J. Xing, J. Chromatogr. A 978 (2002) 37.
27. Z. Zeng, W. Qiu, Z. Huang, Anal. Chem. 73 (2001) 2429.
28. J. L. Glajch, J. J. Kirkland, J. Koehler, J. Chromatogr. 384 (1987) 81.
29. Wehrli, J. C. Hildenbrand, H. P. Keller, R. Stampfli, R. W. Frei, J. Chromatogr. 149 (1978) 199.

30. L. Fang, S. Kulkarni, K. Alhooshani, A. Malik, Anal. Chem. 79 (2007) 9441.
31. M. Liu, Y. Liu, Z. Zeng, T. Peng, J. Chromatogr. A 1108 (2006) 149.
32. X. Li, J. Gao, Z. Zeng, Anal. Chim. Acta 590 (2007) 26.
33. L. M. Wei, Q. Y. Ou, J. B. Li, Chin. Chem. Letters 15 (2004) 1127.
34. L. Armelao, M. Fabrizio, S. Gross, A. Martucci, E. Tondello, J. Mater. Chem. 10 (2000) 1147.
35. J. D. Hayes, A. Malik, J. Chromatogr. B. 695 (1997) 3.
36. C. J. Brinker, G. W. Scherer, Sol-Gel Science: The Chemistry and Physics of Sol-Gel Processing, Academic Press, San Diego, Calif., 1990.
37. J. Livage, M. Henry, C. Sanchez, Prog. Solid State Chem. 18 (1988) 259.
38. R. Doong, S. Chang, Anal. Chem. 72 (2000) 3647.
39. Y. Hu, Y. Zheng, F. Zhu, G. Li, J. Chromatogr. A 1148 (2007) 16.
40. G. Jiang, M. Huang, Y. Cai, J. Jv, Z. Zhao, J. Chromatogr. Sci. 44 (2006) 324.
41. D. R. Stoll, P. W. Can, J. Am. Chem. Soc. 127 (2005) 5034.
42. F. D. Antia, C. Horvath, J. Chromatogr. 435 (1988) 1.
43. B. Yan, J. Zhao, J. S. Brown, J. Blackwell, P. W. Carr, Anal. Chem. 72 (2000) 1253.
44. J. Clark, Pharm. Technol. Europe 16 (2004) 41.

What is claimed is:

1. A solid-phase microextraction material for preconcentration of trace analytes in a sample, wherein a surface of the solid-phase microextraction material is coated with surface-bonded sol-gel germania triblock polymer that forms the stationary phase for the microextraction of the analytes; wherein the sol-gel germania triblock polymer comprises sol-gel germania triblock poly(ethylene oxide)-block-poly(propylene oxide)-block-poly(ethylene oxide) having the following chemical structure:

wherein n, x, y, and z are, independently, an integer$\geq$1.

2. The solid-phase microextraction material of claim 1, wherein the sol-gel germania triblock polymer is made from a sol-gel precursor that forms upon hydrolysis.

3. The solid-phase microextraction material of claim 1, wherein the sol-gel germania triblock polymer is made from a sol-gel precursor that is tetra-n-butoxygermane (TNBG).

4. The solid-phase microextraction material of claim 1, wherein the solid-phase microextraction material comprises fused silica.

5. The solid-phase microextraction material of claim 1, wherein the sol-gel germania triblock polymer is chemically stable at a pH of about 0 and/or about 14.

6. The solid-phase microextraction material of claim 1, wherein the sol-gel germania triblock polymer is chemically stable at a temperature of about 200° C.

7. The solid-phase microextraction material of claim 1, wherein the analyte is selected from polycyclic aromatic hydrocarbon (PAH), ketone, alcohol, phenol, or amine.

8. A microextraction capillary comprising the solid-phase microextraction material of claim 1, wherein an inner surface of the microextraction capillary is coated with surface-bonded sol-gel germania triblock polymer.

9. A method for preconcentration of trace analytes in a sample, comprising:
contacting a sample containing an analyte with the solid-phase microextraction material of claim 1; and
desorbing the analyte from the sol-gel germania triblock polymer.

10. The method of claim 9, further comprising analyzing the analyte using gas chromatography (GC), capillary electrophoresis, inductively coupled plasma mass spectrometry, and/or high-performance liquid chromatography (HPLC).

11. The method of claim 9, wherein the sol-gel germania triblock polymer comprises germania triblock poly(ethylene oxide)-block-poly(propylene oxide)-block-poly(ethylene oxide) having the following chemical structure:

wherein n, x, y, and z are, independently, an integer >=1.

12. The method of claim 9, wherein the solid-phase microextraction material comprises fused silica.

13. The method of claim 9, performed at a pH of about 0 or about 14, or at any pH in between 0 and 14.

14. The method of claim 9, wherein the sol-gel germania triblock polymer coating is chemically stable at a temperature of 200° C.

15. The method of claim 9, wherein the analyte is selected from polycyclic aromatic hydrocarbon (PAH), ketone, alcohol, phenol, or amine.

16. A method of making the microextraction capillary of claim 8, comprising:
preparing a sol solution comprising tetra-n-butoxygermane;
processing the sol solution to form a sol-gel extraction medium;
filling a capillary with the sol-gel extraction medium wherein the sol-gel extraction medium chemically binds to the inner walls of the capillary to form sol-gel germania triblock polymer-coated capillary; and
purging the capillary of unbound sol-gel extraction medium.

17. The method of claim 16, wherein the sol solution further comprises hydroxy-terminated triblock polymer.

18. The method of claim 17, wherein the hydroxy-terminated triblock polymer is poly(ethylene oxide)-block-poly(propylene oxide)-block-poly(ethylene oxide) having the following chemical structure:

wherein n, x, y, and z are, independently, an integer >=1.

19. The method of claim 17, wherein the sol-gel germania triblock polymer is made from a sol-gel precursor that forms upon hydrolysis.

* * * * *

UNITED STATES PATENT AND TRADEMARK OFFICE
CERTIFICATE OF CORRECTION

PATENT NO. : 9,528,921 B2
APPLICATION NO. : 13/641640
DATED : December 27, 2016
INVENTOR(S) : Abdul Malik and Scott S. Segro It is certified that error appears in the above-identified patent and that said Letters Patent is hereby corrected as shown below:

In the Specification

Column 2,
Lines 27-30, "In one embodiment, the triblock polymer is poly(ethylene oxide)-block-poly(propylene oxide)-block-poly(ethylene oxide) (PEO-PPO-PEO, also known as poloxamer), which has the following structure:" should read --In one embodiment, the triblock polymer, covalently bonded to the sol-gel germania network, is poly(ethylene oxide)-block-poly(propylene oxide)-block-poly(ethylene oxide) (PEO-PPO-PEO, also known as poloxamer), covalently bonded to the sol-gel germania network which has the following structure:--.
Lines 30-31, "cheaned" should read --cleaned--.

Columns 3-4,
Lines 33-52,

" 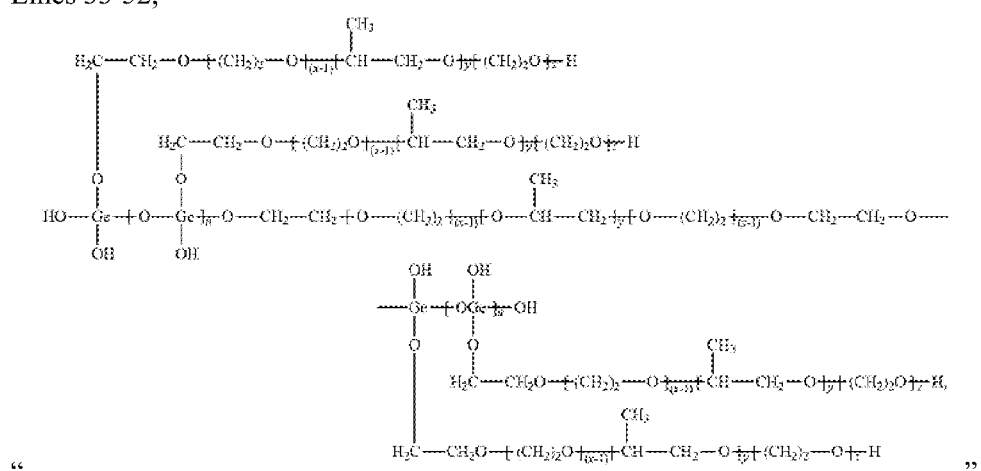 "

Signed and Sealed this
Fourteenth Day of November, 2017

Joseph Matal
*Performing the Functions and Duties of the
Under Secretary of Commerce for Intellectual Property and
Director of the United States Patent and Trademark Office* should read --
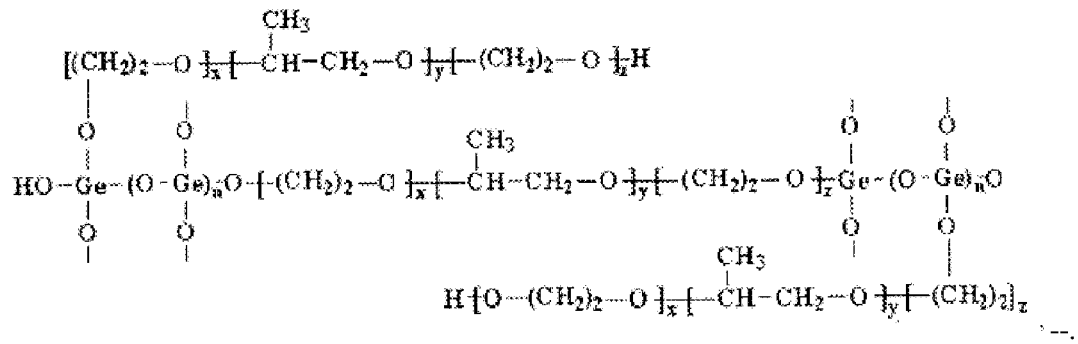
Column 6,
Lines 35-40, " 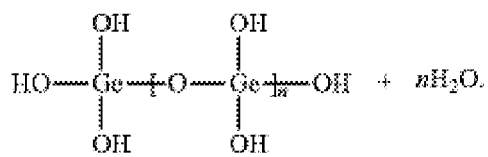 " should read
-- 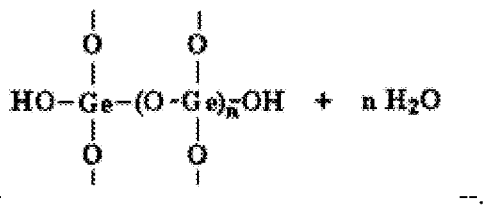 --.
Line 41, "hydroxyl-terminated" should read --hydroxy-terminated--.
Columns 5-8,
Lines 45-10,
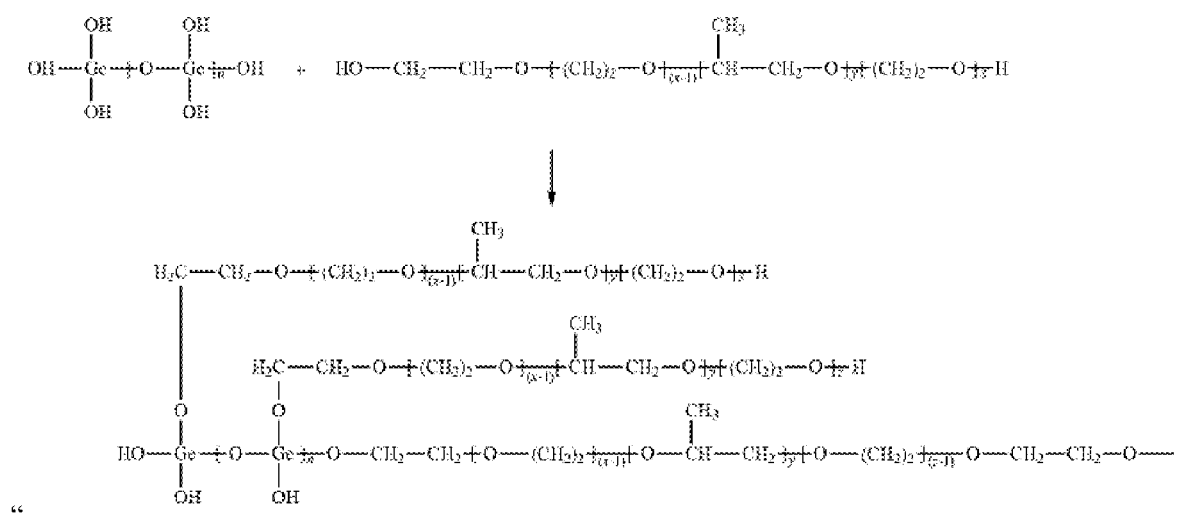

CERTIFICATE OF CORRECTION (continued)
U.S. Pat. No. 9,528,921 B2

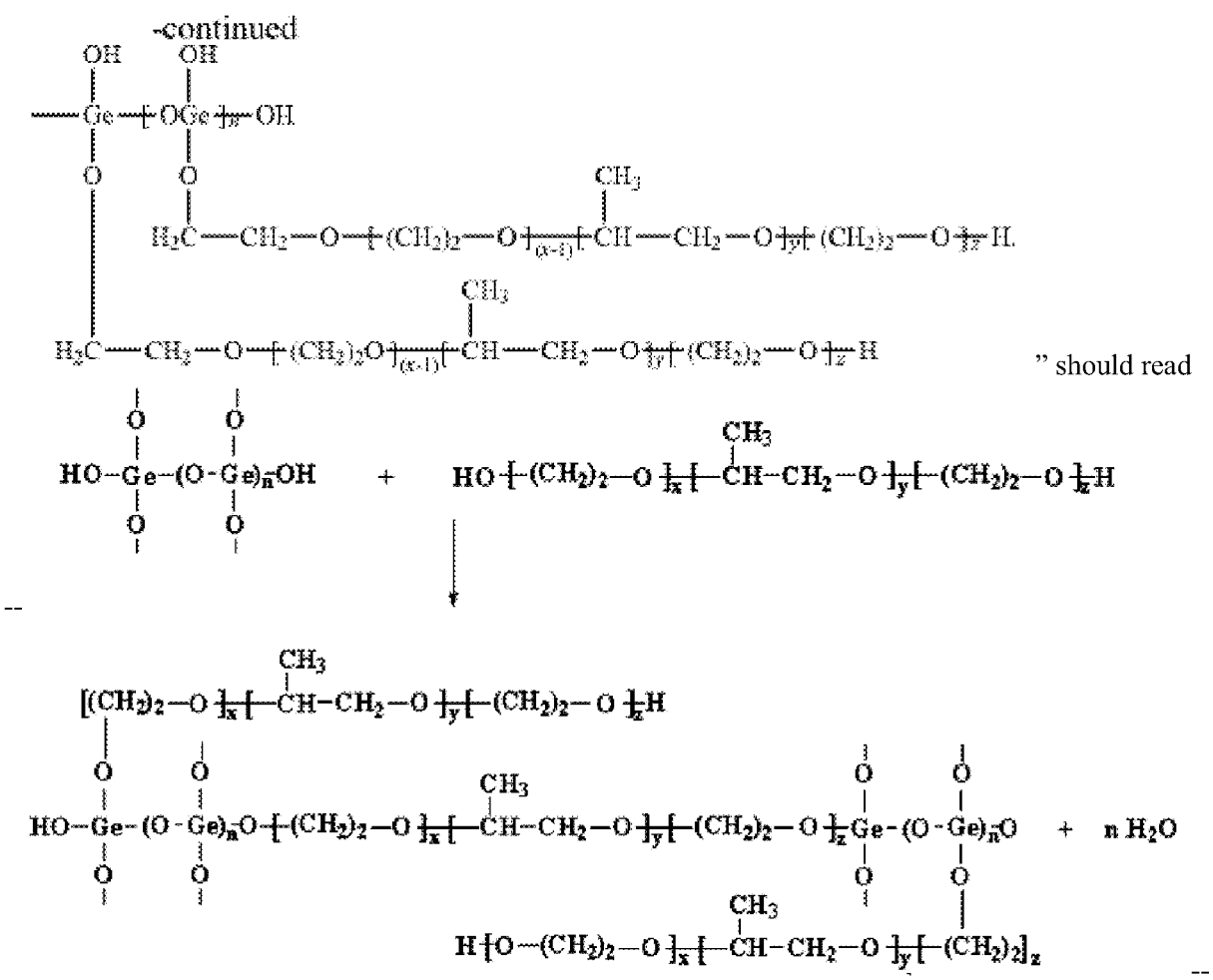

" should read

--

Columns 9-10,
Lines 1-67,
"

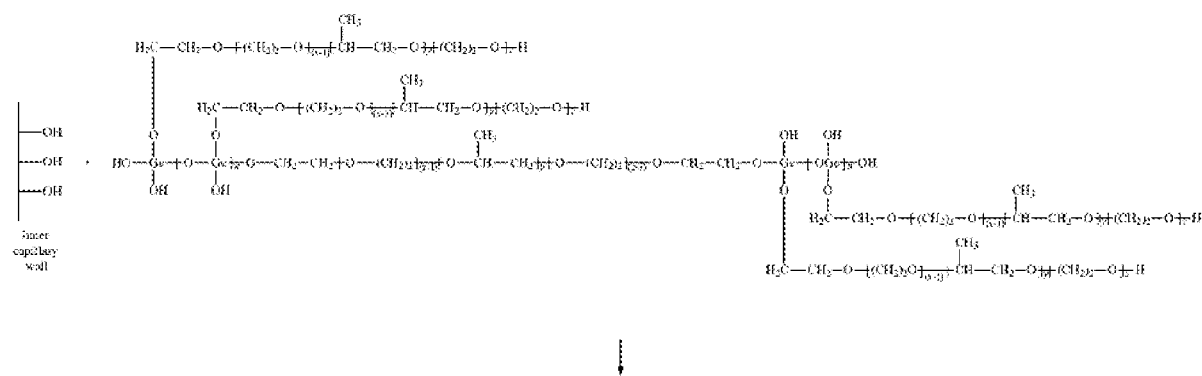

CERTIFICATE OF CORRECTION (continued)
U.S. Pat. No. 9,528,921 B2 surface-bonded sol-gel germania tri-block polymer coating

" should read

--

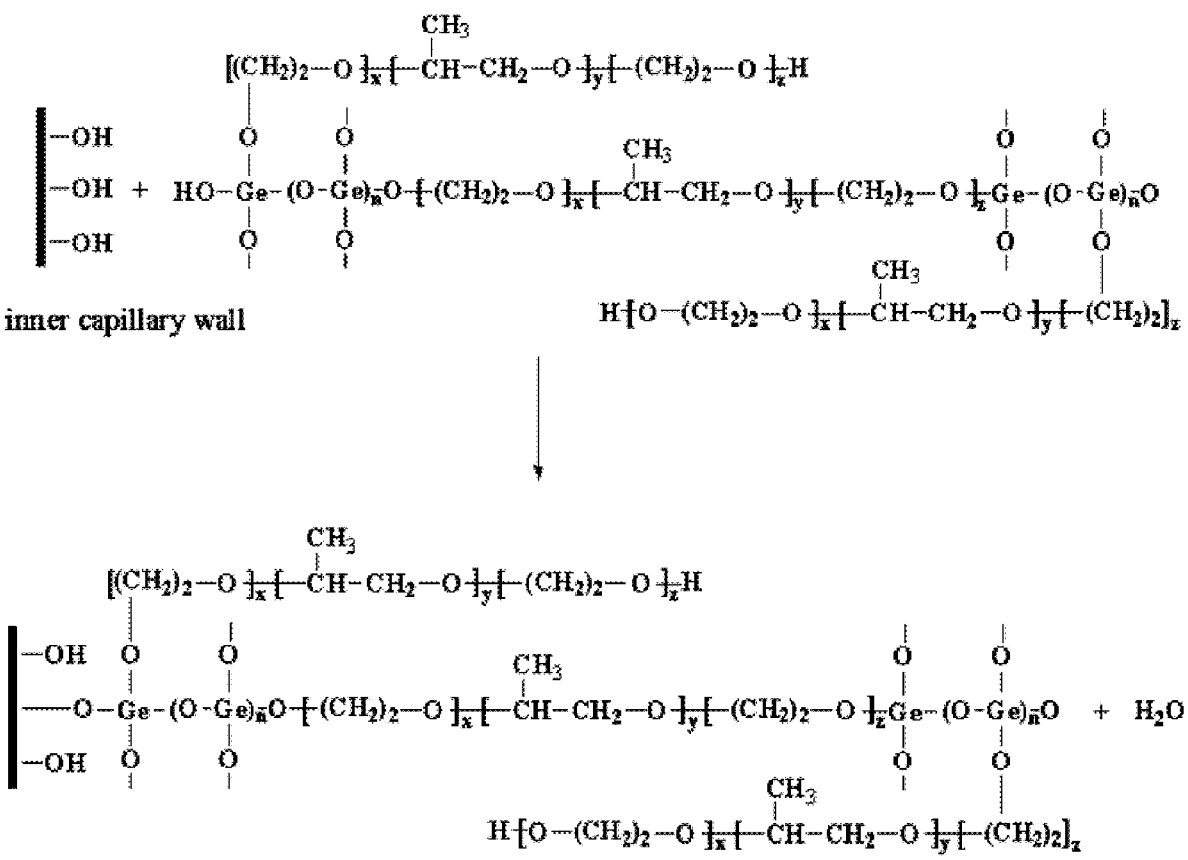

--.

Columns 11-12,
Lines 1-67,

"
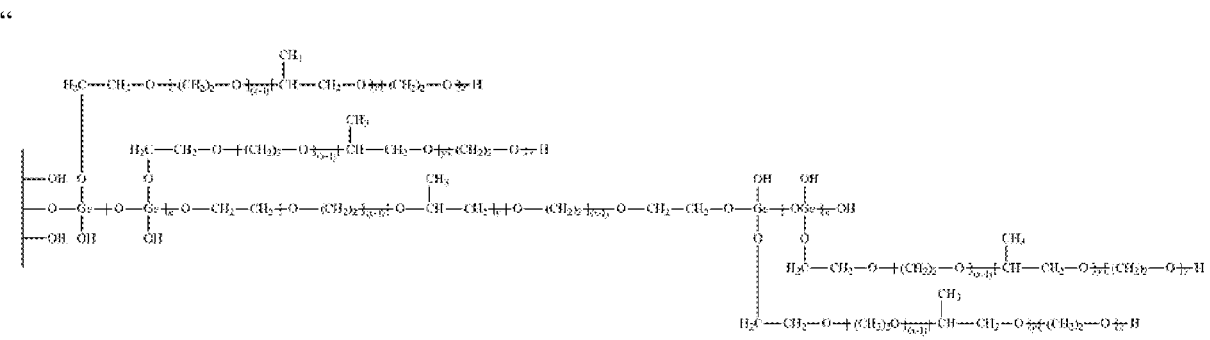
" should read --In Scheme 2, n, x, y, and z are, independently, an integer >=1.--.
Column 18,
Line 29, "(2005)" should read --(2005.)--.
In the Claims
Column 20,
Line 62, "Can," should read --Carr,--.